(12) United States Patent
Yang (10) Patent No.: US 12,318,628 B2
(45) Date of Patent: Jun. 3, 2025

(54) ADJUVANT NAIL TREATMENT DEVICE

(71) Applicant: Shenzhen Haige Cross Border Technology Co., Ltd., Shenzhen (CN)

(72) Inventor: Yunhang Yang, Shenzhen (CN)

(73) Assignee: Shenzhen Haige Cross Border Technology Co., Ltd., Shenzhen (CN)

( * ) Notice: Subject to any disclaimer, the term of this patent is extended or adjusted under 35 U.S.C. 154(b) by 0 days.

(21) Appl. No.: 18/365,248

(22) Filed: Aug. 4, 2023

(65) Prior Publication Data

US 2023/0372732 A1    Nov. 23, 2023

(51) Int. Cl.
*A61N 5/06* (2006.01)
*A61N 5/00* (2006.01)

(52) U.S. Cl.
CPC .... *A61N 5/0624* (2013.01); *A61H 2201/5043* (2013.01); *A61H 2201/5097* (2013.01); *A61H 2205/067* (2013.01); *A61N 2005/005* (2013.01); *A61N 2005/0628* (2013.01); *A61N 2005/0633* (2013.01); *A61N 2005/0645* (2013.01); *A61N 2005/0652* (2013.01);
(Continued)

(58) Field of Classification Search
CPC . A61B 18/20–18/28; A61H 2201/5043; A61H 2201/5097; A61H 2205/067; A61N 2005/005; A61N 2005/0628; A61N 2005/0633; A61N 2005/0643; A61N 2005/0645; A61N 2005/0652; A61N 2005/0654; A61N 2005/0659; A61N 2005/0662; A61N 2005/0663; A61N 5/0616; A61N 5/062; A61N 5/0624

USPC .................................. 606/2–19; 607/88–94
See application file for complete search history.

(56) References Cited

U.S. PATENT DOCUMENTS

| 2002/0103423 A1* | 8/2002 | Chin ................... A61B 5/6833 600/323 |
| 2004/0152051 A1* | 8/2004 | Craig .................. A61C 19/066 433/140 |

(Continued)

FOREIGN PATENT DOCUMENTS

CN          219612315 U  *  8/2023

*Primary Examiner* — Jonathan T Kuo
*Assistant Examiner* — Vynn V Huh
(74) *Attorney, Agent, or Firm* — Fideli Law PLLC; Qiang Li (57) ABSTRACT

The present disclosure discloses an adjuvant nail treatment device, including a lower shell component and an upper shell component; an irradiation control component and a display screen, which are fixedly arranged in the upper shell component, wherein the irradiation control component includes a circuit board fixedly arranged in the upper shell component, and the display screen penetrates through the upper shell component; the irradiation control component includes a photosensitive lamp group, a therapy lamp group, and a photosensor device which are respectively fixedly arranged on the circuit board and respectively penetrate through a support in the upper shell component; a photosensitive component, fixedly arranged on the lower shell component and located below the irradiation control component, wherein the photosensitive component reflects light emitted by the photosensitive lamp group to the photosensor device; and a battery component, fixedly arranged in the lower shell component.

17 Claims, 6 Drawing Sheets

(52) U.S. Cl.
CPC ............... *A61N 2005/0654* (2013.01); *A61N 2005/0659* (2013.01); *A61N 2005/0663* (2013.01)

(56) References Cited

U.S. PATENT DOCUMENTS

| | | | | |
|---|---|---|---|---|
| 2008/0097414 | A1* | 4/2008 | Li | A61N 5/0603 |
| | | | | 606/15 |
| 2008/0194928 | A1* | 8/2008 | Bandic | A61B 5/443 |
| | | | | 600/306 |
| 2009/0234270 | A1* | 9/2009 | Loebel | A61K 31/045 |
| | | | | 604/20 |
| 2012/0109265 | A1 | 5/2012 | Shanks et al. | |
| 2013/0172961 | A1 | 7/2013 | Enemaerke | |
| 2015/0062078 | A1* | 3/2015 | Christman | A61B 5/6897 |
| | | | | 345/174 |
| 2016/0022213 | A1* | 1/2016 | Lee | A61B 5/6838 |
| | | | | 600/300 |
| 2016/0038055 | A1* | 2/2016 | Wheeler | A61B 5/7225 |
| | | | | 600/301 |
| 2018/0035943 | A1* | 2/2018 | Shemesh | A61B 5/0205 |
| 2021/0145363 | A1* | 5/2021 | Cho | A61B 5/70 |
| 2021/0282652 | A1* | 9/2021 | Donnelly | A61B 5/11 |
| 2023/0103406 | A1* | 4/2023 | Meehan | A61B 5/6826 |
| | | | | 600/310 |
| 2023/0226068 | A1 | 7/2023 | Schuele | |

* cited by examiner

ADJUVANT NAIL TREATMENT DEVICE

TECHNICAL FIELD

The present disclosure relates to the technical field of health care equipment, and particularly relates to an adjuvant nail treatment device.

BACKGROUND

Onychomycosis, also referred to as tinea unguium, is a lesion caused by invasion of the nail plates by dermatophytes and is highly contagious. At present, there are many therapies for the onychomycosis, but their therapeutic effects are poor. For example, oral antifungal drugs such as griseofulvin, fluconazole, and itraconazole (sporanox) have low solubility in water, low dissolution, and rapid absorption and metabolism. Because these drugs would not play an antibacterial role until they reach a nail plate infested with fungi, the dosage of drugs is large and the medication cycle is long, causing a burden on the liver and kidney of a patient. Externally applied drugs are convenient to use, have less side effects, and are more acceptable to patients. However, before use of an externally applied drug, a nail needs to be cut loose with a knife and then applied with the drug. Since the structure of the nail itself blocks the penetration of externally applied drug, the drug function is difficult to exert, which easily causes recurrent attacks of the onychomycosis. In order to effectively eradicate the onychomycosis, it is necessary to carry out adjuvant treatment during drug treatment. Existing adjuvant treatment equipment for onychomycosis usually performs irradiation using blue rays and infrared rays, which can kill fungi and enhance the treatment effect by the irradiation of the blue rays and the infrared rays. However, the existing adjuvant treatment equipment for onychomycosis cannot adaptively match irradiation time and light intensity according to sizes of different nails. Therefore, an adjuvant nail treatment device is provided to solve the problem that adjuvant treatment equipment for onychomycosis cannot match corresponding irradiation time and light intensity according to sizes of different nails in the prior art.

SUMMARY

One objective of the present disclosure is to provide an adjuvant nail treatment device, so as to solve the problem that adjuvant treatment equipment for onychomycosis cannot match corresponding irradiation time and light intensity according to sizes of different nails in the prior art.

The adjuvant nail treatment device of the present disclosure can be achieved by the following technical solutions:

The adjuvant nail treatment device of the present disclosure includes a lower shell component and an upper shell component, wherein the lower shell component and the upper shell component are arranged in a relatively movable manner and ca be clamped to each other; an irradiation control component, fixedly arranged in the upper shell component, wherein the irradiation control component includes a circuit board, a photosensitive lamp group, a therapy lamp group, and a photosensor device; the circuit board is fixedly arranged in the upper shell component and is electrically connected to the photosensitive lamp group, the therapy lamp group, and the photosensor device respectively; the photosensitive lamp group, the therapy lamp group, and the photosensor device are respectively fixedly arranged on the circuit board and respectively penetrate through a support in the upper shell component; the photosensitive lamp group emits photosensitive light; the therapy lamp group emits blue rays and infrared rays; the photosensor device receives the emitted photosensitive light; a display screen, fixedly arranged in the upper shell component and penetrating through the upper shell component, wherein the display screen is electrically connected to the circuit board and sets real-time displaying and touch-control functions; a photosensitive component, fixedly arranged on the lower shell component and located below the irradiation control component, wherein the photosensitive component reflects the light emitted by the photosensitive lamp group to the photosensor device; a vibration motor, arranged in the upper shell component and electrically connected to the circuit board, wherein the vibration motor reminds a user of the start and end of adjuvant treatment in a vibration manner; a battery component, fixedly arranged in the lower shell component and electrically connected to the circuit board, wherein the battery component respectively supplies power to the irradiation control component, the display screen, and the vibration motor; and a wireless charging coil, arranged in the lower shell component and electrically connected to the circuit board, wherein the wireless charging coil provides wireless charging for the battery component.

Preferably, the lower shell component includes a lower shell and a lower support; the lower shell is a hollow cavity; the lower support sis fixedly arranged on the lower shell to form a closed cavity; the battery component and the wireless charging coil are respectively fixedly arranged in the cavity encircled by the lower shell and the lower support; and the photosensitive component is fixedly arranged on the lower support.

Preferably, rotating shafts are arranged on two opposite sides of the lower shell; and the upper shell component is movably arranged on the lower shell component through the rotating shafts.

Preferably, the upper shell component includes an upper shell and an upper support; the upper shell is a hollow cavity; the upper support sis fixedly arranged on the upper shell to form a closed cavity; and the irradiation control component and the display screen are respectively fixedly arranged in the cavity encircled by the upper shell and the upper support.

Preferably, a cover plate is arranged on the upper shell; the position of the cover plate corresponds to the position of the display screen; and a displayed content of the display screen can be observed through the cover plate, and a touch-control operation can be performed on the display screen.

Preferably, a plurality of heat dissipation holes are formed in the upper shell in a penetrating manner, and heat in the upper shell component is dissipated through the plurality of heat dissipation holes.

Preferably, the irradiation control component further includes a circuit board charging interface, arranged on a side edge of the circuit board and penetrating through the upper shell component; and the charging interface provides wired charging for the battery component.

Preferably, the charging interface adopts a Micro USB interface or a Type-C interface.

Preferably, the circuit board is further provided with a wireless communication module; wireless connection to an electronic terminal is achieved through the wireless communication module; and the device is wirelessly controlled through an application or a mini program on the electronic device.

Preferably, the wireless communication module is one or more of a Bluetooth wireless communication module, a WiFi wireless communication module, a fourth-generation (4G) wireless communication module, and a fifth-generation (5G) wireless communication module.

Preferably, the photosensitive lamp group includes a plurality of white light sensitive light-emitting diodes (LEDs), and the plurality of white light sensitive LEDs are uniformly distributed on the circuit board.

Preferably, the therapy lamp group includes a plurality of blue LEDs and a plurality of infrared LEDs.

Preferably, an emission wavelength of the blue LEDs ranges from 400 nm to 500 nm.

Preferably, an emission wavelength of the infrared LEDs ranges from 850 nm to 950 nm.

Compared with the prior art, the adjuvant nail treatment device of the present disclosure has the beneficial effects below:

According to the adjuvant nail treatment device of the present disclosure, a nail of a user is fixed by the mutual clamping effect of the lower shell component and the upper shell component; the photosensitive lamp group emits light to irradiate the nail of the user on the photosensitive component; the photosensitive component reflects remaining light to the photosensor device; the light is processed through the circuit board to determine a size of the nail of the user; the corresponding irradiation time and light intensity of the therapy lamp group are then adjusted through the circuit board, so that the following problem is effectively solved: adjuvant treatment equipment for onychomycosis cannot match corresponding irradiation time and light intensity according to sizes of different nails in the prior art.

By the arrangement of the vibration motor, the adjuvant nail treatment device of the present disclosure effectively reminds a user of the start and end of the adjuvant treatment. Meanwhile, due to the two charging manners: the charging interface and the wireless charging coil, a customer can select the charging manner according to an actual need or a personal preference, which improves the experience of the customer to a certain extent.

BRIEF DESCRIPTION OF THE DRAWINGS

In order to explain the technical solutions of the embodiments of the present disclosure more clearly, the following will briefly introduce the accompanying drawings used in the embodiments. It should be understood that the drawings in the following description only illustrate some embodiments of the present disclosure and thus shall not be deemed as limiting the scope. Those of ordinary skill in the art can obtain other related drawings based on these drawings without creative work.

Numerals in the drawings: 11: lower shell component; 111: lower shell; 1111: rotating shaft; 1112: notch; 112: lower support; 12: upper shell component; 121: upper shell; 1211: cover plate; 1212: heat dissipation hole; 1213: interface hole; 122: upper support; 13: irradiation control component; 131: circuit board; 132: photosensitive lamp group; 133: therapy lamp group; 134: photosensor device; 135: charging interface; 14: photosensitive component; 141: photosensitive board; 142: separator plate; 15: display screen; 16: vibration motor; 17: battery component; 18: wireless charging coil; and 181: heat isolation layer.

DETAILED DESCRIPTION OF THE EMBODIMENTS

In order to make the objectives, technical solutions and advantages of the embodiments of the present disclosure clearer, the technical solutions in the embodiments of the present disclosure will be described clearly and completely below in combination with the drawings in the embodiments of the present disclosure. Obviously, the embodiments described herein are part of the embodiments of the present disclosure, not all the embodiments. The components of the embodiments of the present disclosure generally described and shown in the drawings here can be arranged and designed in a variety of different configurations.

Therefore, the following detailed description for the embodiments of the present disclosure provided in the accompanying drawings is not intended to limit the scope of the claimed present disclosure, but merely represents selected embodiments of the present disclosure. All other embodiments obtained by those of ordinary skill in the art based on the embodiments in the present disclosure without creative work shall fall within the protection scope of the present disclosure.

Referring to FIG. 1 to FIG. 6, an adjuvant nail treatment device of the present disclosure mainly includes a lower shell component 11, an upper shell component 12, an irradiation control component 13, a photosensitive component 14, a display screen 15, a vibration motor 16, a battery component 17, and a wireless charging coil 18. The lower shell component 11 and the upper shell component 12 are both hollow cavities. The upper shell component 12 is movably arranged on the lower shell component 11 and can rotate relative to the lower shell component 11, and the upper shell component and the lower shell component are clamped. A nail is placed on the photosensitive component 14 through a notch 1112 between the lower shell component 11 and the upper shell component 12. The irradiation control component 13 is fixedly arranged in the upper shell component 12 and is electrically connected to the display screen 15, the vibration motor 16, the battery component 17, and the wireless charging coil 18, respectively. The photosensitive component 14 is fixedly arranged on the lower shell component 11 and located below the irradiation control component 13. The photosensitive component performs a photosensitive operation on light emitted by the irradiation control component 13, thereby causing the irradiation control component 13 to determine a size of the nail placed on the photosensitive component 14 and determine matching irradiation time and light intensity. The display screen 15 is fixedly arranged in the upper shell component 12 and penetrates through the upper shell component 12, and is configured to set real-time displaying and touch-control functions. The vibration motor 16 is arranged in the upper shell component 12 and is configured to remind a user of the start and end of adjuvant treatment in a vibration manner.

The battery component 17 and the wireless charging coil 18 are fixedly arranged in the lower shell component 11, respectively. The battery component 17 supplies power to the radiation control component 13, the display screen 15, and the vibration motor 16, respectively. The wireless charging coil 18 tightly abuts against a shell of the lower shell component 11, facilitating the wireless charging coil 18 to provide wireless charging for the battery component 17.

Figure 1:
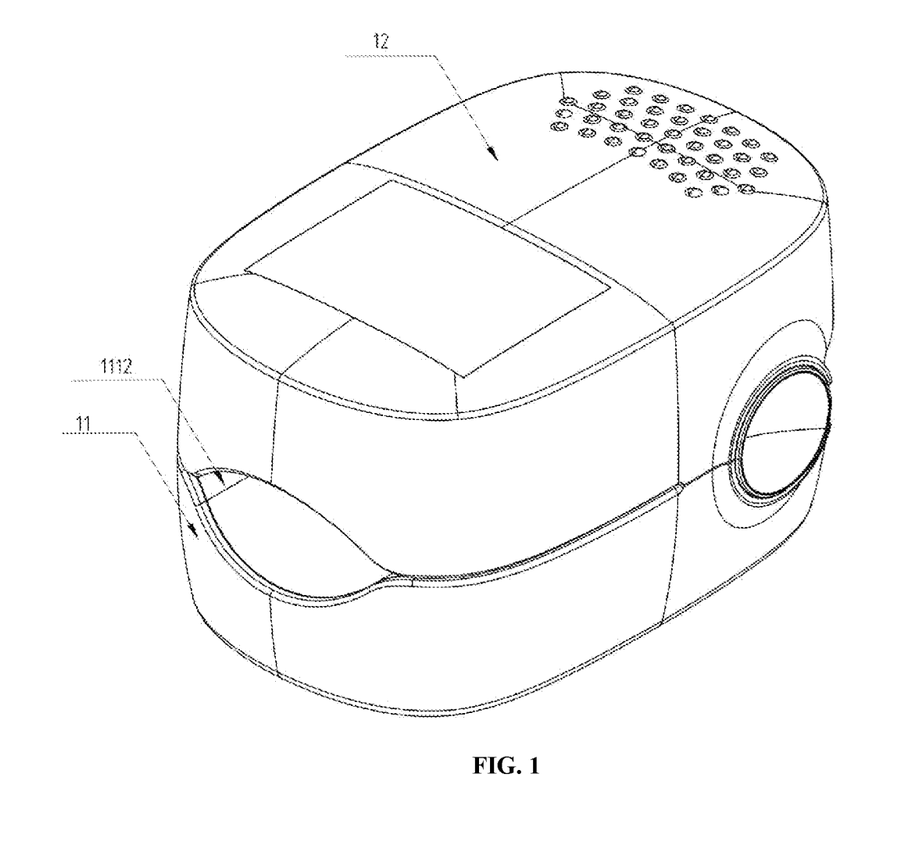
FIG. 1 is a schematic structural diagram of an adjuvant nail treatment device according to the present disclosure.
Figure 2:
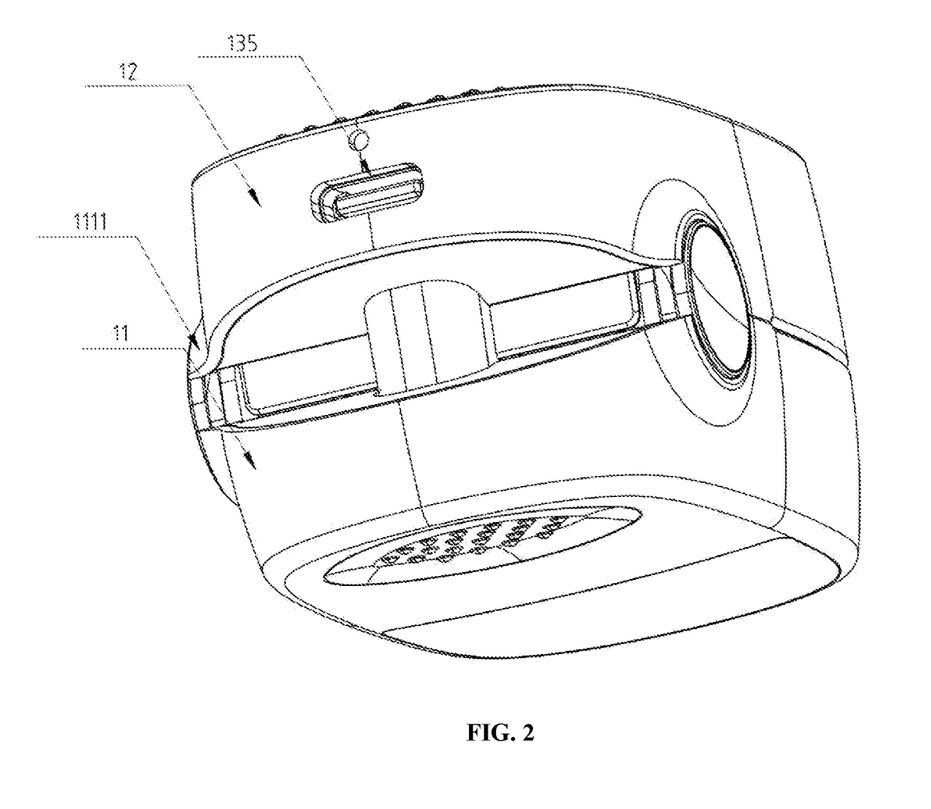
FIG. 2 is a schematic structural diagram of the adjuvant nail treatment device shown in FIG. 1 according to the present disclosure in another view.
Figure 3:
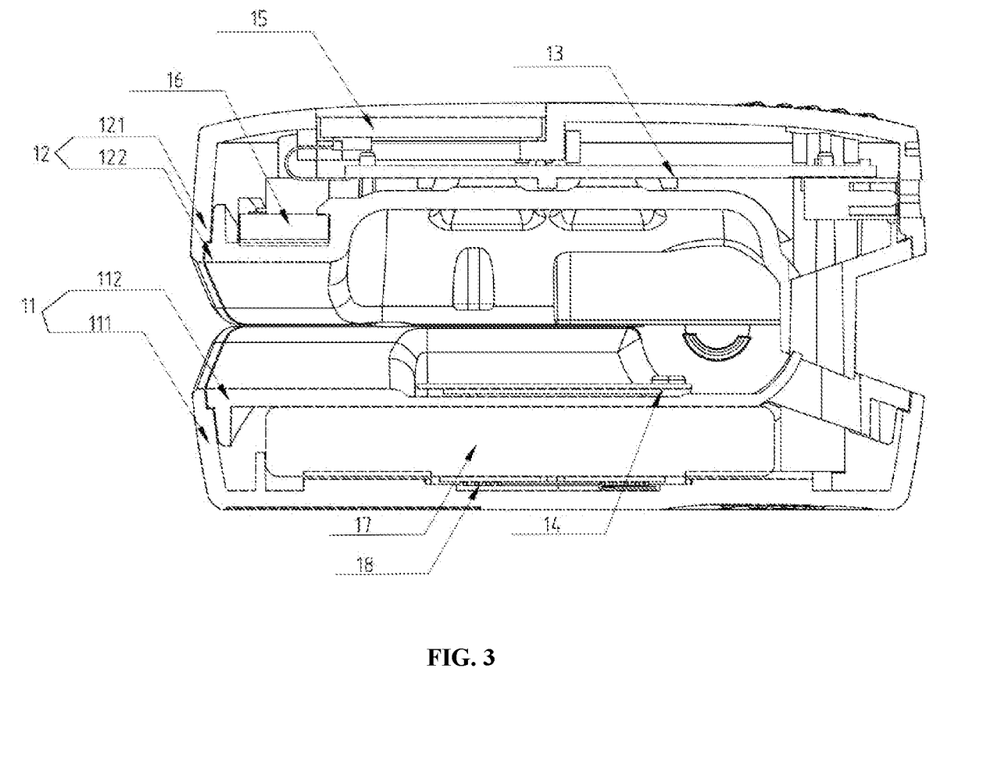
FIG. 3 is a schematic diagram of sectional connection of the adjuvant nail treatment device shown in FIG. 1 according to the present disclosure.
Figure 4:
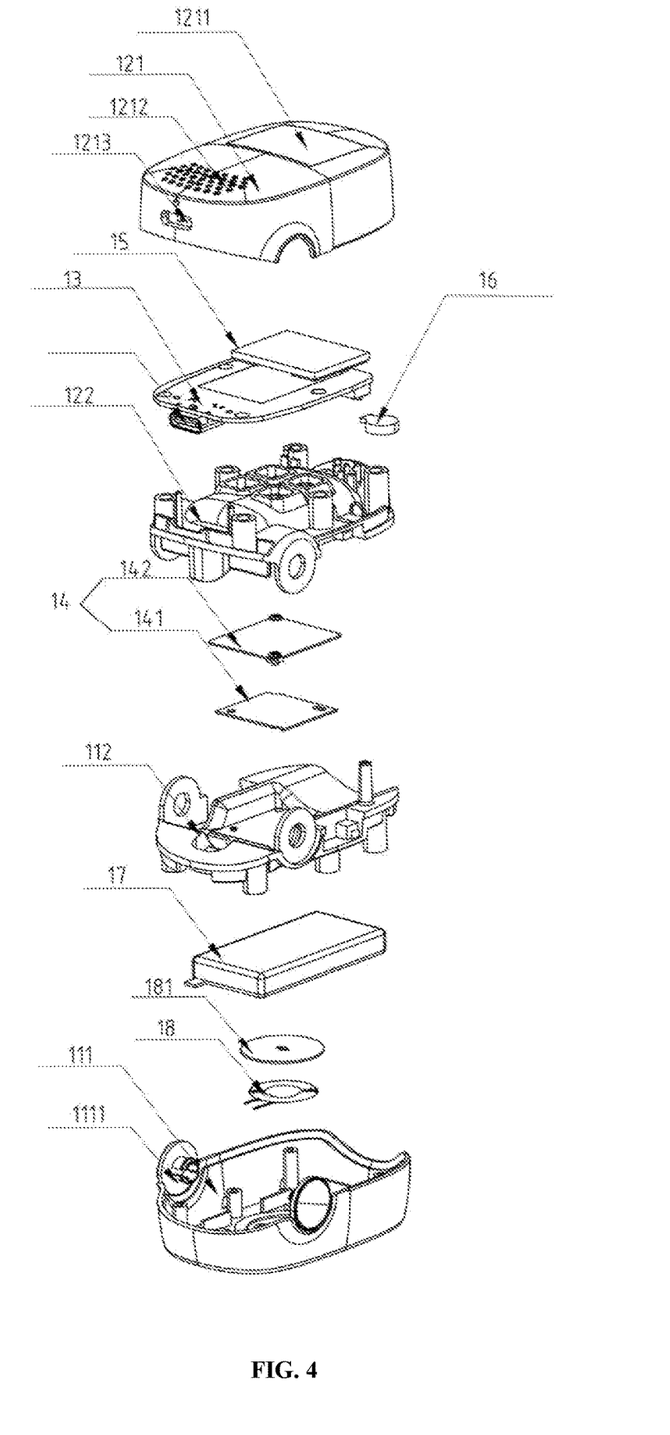
FIG. 4 is an exploded structural diagram of the adjuvant nail treatment device shown in FIG. 1 according to the present disclosure.
Figure 5:
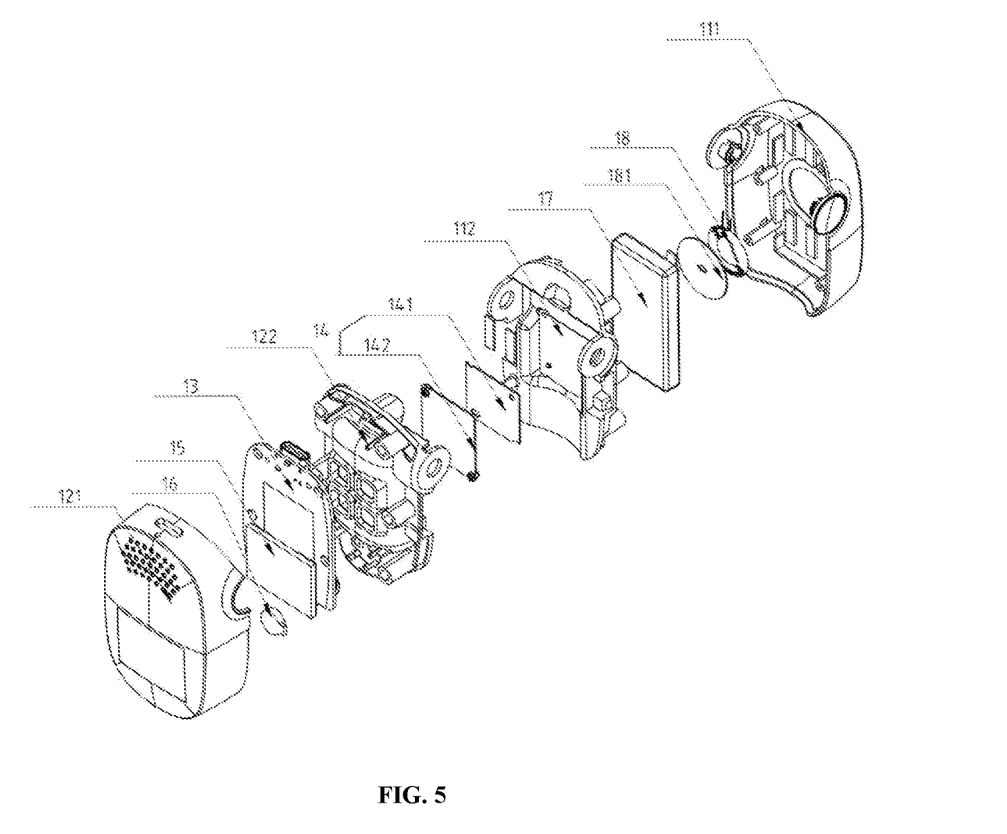
FIG. 5 is an exploded structural diagram of the adjuvant nail treatment device shown in FIG. 1 according to the present disclosure in another view, including an irradiation control component.

Referring to FIG. 3 to FIG. 5, in this embodiment, the lower shell component 11 includes a lower shell 111 and a lower support 112; the lower shell 111 is a hollow cavity; the lower support 112 is fixedly arranged on the lower shell 111 to form a closed cavity; the battery component 17 and the wireless charging coil 18 are respectively fixedly arranged in the cavity encircled by the lower shell 111 and the lower support 112; the photosensitive component 14 is fixedly arranged on the lower support 112; and the lower support 112 fixedly supports the photosensitive component 14. Specifically, rotating shafts 1111 are arranged on two opposite sides of the lower shell 111, and the upper shell component 12 is movably arranged on the lower shell component 11 through the rotating shafts 1111. Under the action of the rotating shafts 1111, the lower shell component 11 and the upper shell component 12 can be clamped, so that the adjuvant treatment device can be fixed on a nail of a user that needs to be treated.

Referring to FIG. 3 to FIG. 5, in this embodiment, the upper shell component 12 includes an upper shell 121 and an upper support 122; the upper shell 121 is a hollow cavity; the upper support 122 is fixedly arranged on the upper shell 121 to form a closed cavity; the irradiation control component 13 and the display screen 15 are respectively fixedly arranged in the cavity encircled by the upper shell 121 and the upper support 122; and the vibration motor 16 is fixedly arranged on the upper support 122. Specifically, the upper shell 121 is provided with a cover plate 1211; and the position of the cover plate 1211 corresponds to the position of the display screen 15. A displayed content of the display screen 15 can be observed through the cover plate 1211, and a touch-control operation can be performed on the display screen 15. The upper shell 121 is provided with a plurality of heat dissipation holes 1212 and an interface hole 1213 in a penetrating manner. Due to the heat dissipation holes 1212, heat generated by both the irradiation control component 13 and the display screen 15 which are arranged in the upper shell component 12 can be dissipated.

Referring to FIG. 3 to FIG. 6, in this embodiment, the irradiation control component 13 includes a circuit board 131, a photosensitive lamp group 132, a therapy lamp group 133, a photosensor device 134, and a charging interface 135; and the circuit board 131 is fixedly arranged in the upper shell component 12 and is electrically connected to the photosensitive lamp group 132, the therapy lamp group 133, the photosensor device 134, the charging interface 135, the display screen 15, the vibration motor 16, the battery component 17, and the wireless charging coil 18 respectively. A control technology used is the prior art, so a specific control process and product model numbers will not be described in detail. The photosensitive lamp group 132, the therapy lamp group 133, and the photosensor device 134 are respectively fixedly arranged on the circuit board 131 and respectively penetrate through the upper support 122. The photosensitive lamp group 132 emits photosensitive light, and the therapy lamp group 133 emits blue rays and infrared rays at the same time. The rays emitted by the photosensitive lamp group 132 and the therapy lamp group 133 can be transmitted from the upper support 122 to irradiate the nail of the user placed on the photosensitive component 14. The photosensor device 134 can receive light reflected by the photosensitive component 14, so as to determine a size of the nail of the user. The charging interface 135 is arranged on a side edge of the circuit board 131, penetrates through the upper shell component 12 through the interface hole 1213, and is configured to provide wired charging for the battery component 17.

Figure 6:
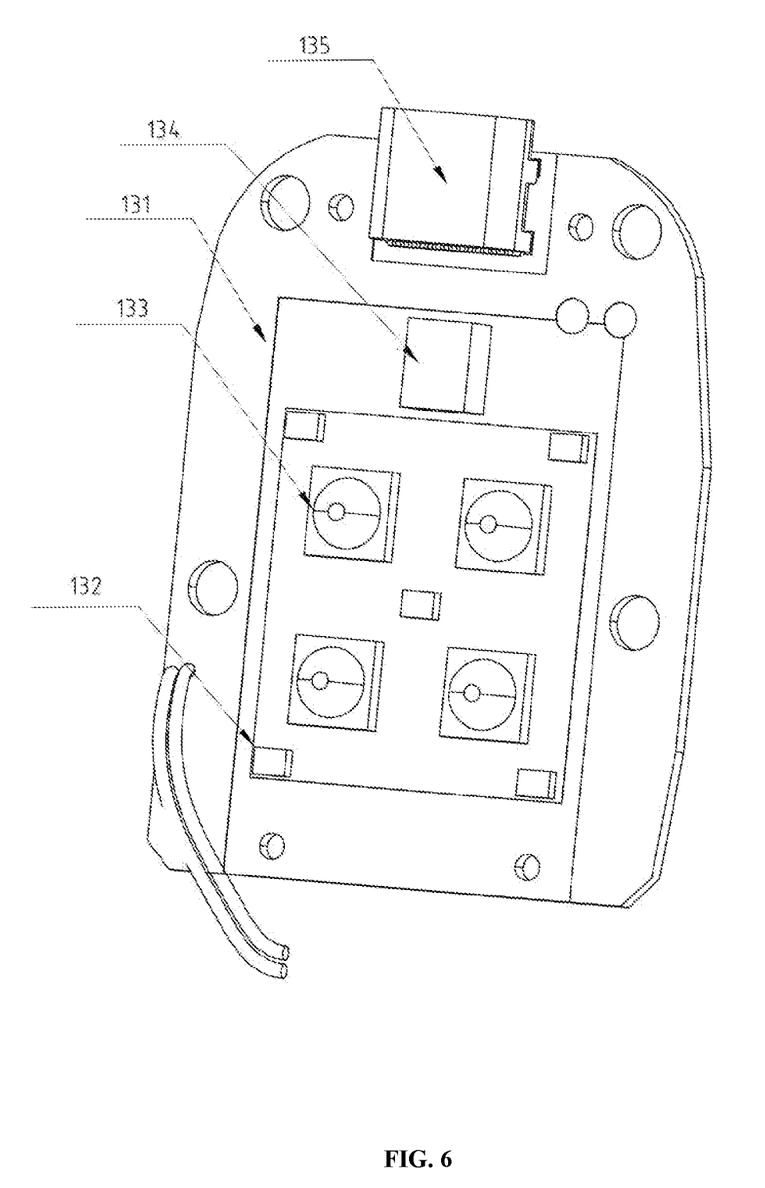
FIG. 6 is a schematic structural diagram of the irradiation control component shown in FIG. 5.

Referring to FIG. 6, in some embodiments, the circuit board 131 may be further provided with a wireless communication module. Wireless connection to an electronic terminal is achieved through the wireless communication module, so that the device is wirelessly controlled through an application or a mini program on the electronic device. Specifically, the wireless communication module is one or more of a Bluetooth wireless communication module, a WiFi wireless communication module, a 4G wireless communication module, and a 5G wireless communication module. Preferably, the wireless communication module adopts the Bluetooth wireless communication module. In this embodiment, the photosensitive lamp group 132 includes a plurality of white light sensitive LEDs, and the plurality of white light sensitive LEDs are uniformly distributed on the circuit board 131. The therapy lamp group 133 includes a plurality of blue LEDs and a plurality of infrared LEDs. A sterilization operation is performed on the nail through the plurality of blue LEDs and the plurality of infrared LEDs. Specifically, an emission wavelength of the blue LEDs ranges from 400 nm to 500 nm. An emission wavelength of the infrared LEDs ranges from 850 nm to 950 nm. Preferably, the emission wavelength of the blue LEDs is 450 nm, and the emission wavelength of the infrared LEDs is 910 nm. The charging interface 135 may be a micro USB interface or a Type-C interface. In this embodiment, the charging interface 135 adopts the Type-C interface.

Referring to FIG. 3 to FIG. 5, in this embodiment, the photosensitive component 14 includes a photosensitive plate 141 and a separator plate 142. The photosensitive plate 141 is arranged on the upper support 122 and is located right below the irradiation control component 13. The photosensitive plate reflects the light emitted by the photosensitive lamp group 132 to the photosensitive sensor device 134. The separator plate 142 is arranged above the photosensitive plate 141 and protects the photosensitive plate 141. Specifically, the separator plate 142 is made of a transparent material, so that the reflected light of the photosensitive plate 141 can be transmitted through the separator plate 142 and received by the photosensitive sensor device 134. In this embodiment, the display screen 15 adopts a touch-control LED display screen. Touch-control settings can be made by touching the display screen 15. The battery module 17 adopts a polymer lithium-ion battery. In this embodiment, in order to reduce the impact of the heat generated by the wireless charging coil 18 on the battery component 17, a heat isolation layer 181 is arranged between the battery component 17 and the wireless charging coil 18, so that transmission of the heat generated by the wireless charging coil 18 to the battery component 17 is alleviated through the heat isolation layer 181. At the same time, the plurality of heat dissipation holes 1212 are formed in positions, opposite to the wireless charging coil 18, on the lower shell 111 in the penetrating manner. The heat generated by both the battery component 17 and the wireless charging coil 18 can be easily dissipated through the heat dissipation holes 1212.

It should be noted that a specific working process of the adjuvant nail treatment device of the present disclosure is as follows: The nail of the user is placed on the photosensitive component 14 through the notch 1112 between the lower shell component 11 and the upper shell component 12; the photosensitive lamp group 13 emits light to irradiate the nail of the user; the photosensitive component 14 reflects the remaining light to the photosensor device 134. The light is processed through the circuit board 131 to determine a size of the nail of the user; the therapy lamp group 133 is adjusted to match corresponding irradiation time and light intensity, thereby completing the adjuvant treatment process.

The above-mentioned embodiments only express several implementation modes of the present disclosure, and their descriptions are more specific and detailed, but they cannot be understood as limiting the patent scope of the present disclosure. It should be noted that those of ordinary skill in the art can further make various transformations and improvements without departing from the concept of the present disclosure, and these transformations and improvements all fall within the protection scope of the present disclosure. Therefore, the protection scope of the patent of the present disclosure shall be subject to the appended claims.

What is claimed is:

1. An adjuvant nail treatment device, comprising:
   a first shell component and a second shell component, wherein the first shell component and the second shell component are arranged in a relatively movable manner and are able to clamp together;
   an irradiation control component, fixedly arranged in the second shell component, including a photosensitive lamp group to emit a first light for nail size detection, a therapy lamp group to emit a second light to a user's nail to enhance fungi treatment effect in the nail, and a photosensor device;
   a photosensitive component, fixedly arranged on the first shell component and facing the irradiation control component for light reflection;
   wherein, after the user's nail is placed between the first shell component and the second shell component, the photosensitive lamp group emits the first light to irradiate the nail; the photosensitive component reflects a portion of the first light to the photosensor device; based on the portion of the first light, the irradiation control component determines a size of the nail; the therapy lamp group adjusts emitting the second light to the nail according to the size of the nail.

2. The adjuvant nail treatment device according to claim 1, wherein the therapy lamp group comprises a plurality of blue LEDs and a plurality of infrared LEDs; and
   the second light includes blue rays and infrared rays.

3. The adjuvant nail treatment device according to claim 2, wherein an emission wavelength of the blue LEDs ranges from 400 nm to 500 nm.

4. The adjuvant nail treatment device according to claim 2, wherein an emission wavelength of the infrared LEDs ranges from 850 nm to 950 nm.

5. The adjuvant nail treatment device according to claim 1, according to claim 1 wherein the first shell component comprises a first shell and a first support; the first shell is a hollow cavity; the first support is fixedly arranged on the first shell to form a closed cavity; the photosensitive component is fixedly arranged on the first support.

6. The adjuvant nail treatment device according to claim 5, wherein rotating shafts are arranged on two opposite sides of the first shell; and the second shell component is movably arranged on the first shell component through the rotating shafts.

7. The adjuvant nail treatment device according to claim 1, wherein the irradiation control component comprises:
   a circuit board, fixedly arranged in the second shell component and electrically connected to the photosensitive lamp group, the therapy lamp group, and the photosensor device respectively,
   wherein the photosensitive lamp group, the therapy lamp group, and the photosensor device are respectively fixedly arranged on the circuit board and respectively penetrate through a support in the second shell component.

8. The adjuvant nail treatment device according to claim 7, wherein the photosensitive lamp group comprises:
   a plurality of white light sensitive light-emitting diodes (LEDs), being uniformly distributed on the circuit board.

9. The adjuvant nail treatment device according to claim 7, further comprising:
   a display screen, fixedly arranged in the second shell component and penetrating through the second shell component,
   wherein the display screen is electrically connected to the circuit board and sets real-time displaying and touch-control functions.

10. The adjuvant nail treatment device according to claim 7, further comprising:
    a vibration motor, arranged in the second shell component and electrically connected to the circuit board, to remind the user of the start and end of adjuvant treatment in a vibration manner.

11. The adjuvant nail treatment device according to claim 7, further comprising:
    a battery component, fixedly arranged in the first shell component and electrically connected to the circuit board, to supply power to the circuit board.

12. The adjuvant nail treatment device according to claim 11, wherein the first shell component comprises: a first shell and a first support; the first shell is a hollow cavity; the first support is fixedly arranged on the first shell to form a closed cavity; and
    the battery component is fixedly arranged in the cavity encircled by the first shell and the first support.

13. The adjuvant nail treatment device according to claim 12, further comprising:
    a wireless charging coil, arranged in the first shell component and electrically connected to the circuit board,
    wherein the wireless charging coil provides wireless charging for the battery component.

14. The adjuvant nail treatment device according to claim 13, wherein the wireless charging coil are respectively fixedly arranged in the cavity encircled by the first shell and the first support.

15. The adjuvant nail treatment device according to claim 14, wherein:
    a plurality of first heat dissipation through-holes are formed on the second shell, and heat in the second shell component is dissipated through the plurality of first heat dissipation through-holes;
    a plurality of second heat dissipation through-holes are formed on the first shell, positioned opposite the wireless charging coil, and heat in the first shell component is dissipated through the plurality of second dissipation through-holes; and
    a heat isolation layer is arranged between the battery component and the wireless charging coil.

16. The adjuvant nail treatment device according to claim 11, wherein the irradiation control component further comprises a circuit board charging interface, arranged on a side edge of the circuit board and penetrating through the second shell component; and the charging interface provides wired charging for the battery component.

17. The adjuvant nail treatment device according to claim 16, wherein the charging interface adopts a Micro USB interface or a Type-C interface.

* * * * *